US008521125B2

(12) United States Patent
Collins et al.

(10) Patent No.: US 8,521,125 B2
(45) Date of Patent: Aug. 27, 2013

(54) ELECTRONIC COMMUNICATION SYSTEMS AND METHODS FOR REAL-TIME LOCATION AND INFORMATION COORDINATION

(75) Inventors: Timothy J. Collins, Homer Glen, IL (US); Esha Bhargava, Astoria, NY (US); Heidi A. Hattendorf, Chicago, IL (US); Graham G. Marshall, Shoreham, NY (US)

(73) Assignee: Motorola Solutions, Inc., Schaumburg, IL (US)

( * ) Notice: Subject to any disclaimer, the term of this patent is extended or adjusted under 35 U.S.C. 154(b) by 57 days.

(21) Appl. No.: 13/112,487

(22) Filed: May 20, 2011

(65) Prior Publication Data

US 2012/0295566 A1 Nov. 22, 2012

(51) Int. Cl.
*H04M 11/04* (2006.01)
(52) U.S. Cl.
USPC .................................... 455/404.1; 455/404.2
(58) Field of Classification Search
USPC .................. 455/457, 517, 63.1, 556.1, 404.2, 455/404.1; 370/338, 466, 278, 315; 705/3, 705/2; 340/573.1, 506
See application file for complete search history.

(56) References Cited

U.S. PATENT DOCUMENTS

| 6,405,213 | B1 * | 6/2002 | Layson et al. ............. 340/539.1 |
| 2006/0003777 | A1 * | 1/2006 | Nonoyama et al. ........... 455/457 |
| 2009/0054735 | A1 * | 2/2009 | Higgins et al. ............... 600/300 |
| 2009/0315717 | A1 * | 12/2009 | Soomro et al. ............. 340/572.1 |
| 2009/0315766 | A1 | 12/2009 | Moe et al. |
| 2010/0185391 | A1 * | 7/2010 | Lee et al. ...................... 701/208 |

FOREIGN PATENT DOCUMENTS

| EP | 2026612 A1 | 2/2009 |
| GB | 2474007 | 4/2011 |

OTHER PUBLICATIONS

International Search Report & Written Opinion dated Jul. 5, 2012 in related case PCT/US2012/037792.

* cited by examiner

*Primary Examiner* — Kiet Doan

(57) ABSTRACT

The present disclosure provides electronic communication systems and methods for real-time location and information coordination between multiple people, such as, for example, in the context of medical emergencies. Specifically, the systems and methods may include a mobile device, a method of operating mobile devices, and a system including a plurality of mobile devices communicatively coupled therebetween for real-time location and information synchronization. In an exemplary embodiment, the systems and methods may be utilized in a medical emergency situation, i.e. for triage, enabling coordination of emergency personnel in an efficient manner. By way of the systems and methods described herein, a common reference point geographically defined, data is gathered with location referenced to the common reference point, and personnel may select patients based on the real-time gathered information.

16 Claims, 5 Drawing Sheets

ELECTRONIC COMMUNICATION SYSTEMS AND METHODS FOR REAL-TIME LOCATION AND INFORMATION COORDINATION

FIELD OF THE INVENTION

The present invention relates generally to electronic communication systems and methods. More particularly, the present invention relates to electronic communication systems and methods for real-time location and information coordination between multiple people, such as, for example, in the context of medical emergencies.

BACKGROUND OF THE INVENTION

In the context of medical emergencies and disasters, triage is a process of determining priority of patients' treatments based on factors such as severity of condition, location, and the like. Advantageously, triage enables efficient rationing of resources when resources are insufficient to treat everyone immediately. For example, triage may be utilized in an emergency situation upon arrival at a disaster scene by emergency personnel including emergency medical technicians (EMT), police, firefighters, and the like. Furthermore, Mobile client devices, such as smart phones, tablet devices, and the like, are proliferating and typically a tool carried by emergency personnel. These mobile client devices provide high-speed wireless connectivity along with computational power rivaling traditional computing devices. Importantly, such mobile client devices have become an indispensable tool for emergency personnel. In the context of emergencies as well as other situations requiring real-time location coordination, there exists a need to couple mobile client devices together for real-time location information and data coordination.

BRIEF SUMMARY OF THE INVENTION

In an exemplary embodiment, a method implemented on a mobile device includes defining a common reference point at a scene; performing a site survey of the scene to gather data and location information; synchronizing the data and location information to a plurality of mobile devices; for each of the plurality of mobile devices, selecting a location from the synchronized data; and for each of the plurality of mobile devices, synchronizing the selection and other data related to the selection with the other mobile devices. The method may further include, for each of the plurality of mobile devices, synchronizing to the common reference point. The performing a site survey may include performing triage to a plurality of patients at different locations at the scene. The performing a site survey may include denoting a location of each of the plurality of patients; and entering data associated with each of the plurality of patients. The performing a site survey further includes taking a picture of each of the plurality of patients. The performing a site survey may further includes associating an identification device with each of the plurality of patients. The defining a common reference point may utilize differential global positioning satellite. The synchronizing to the common reference point may utilize differential global positioning satellite. The synchronizing to the common reference point may utilize dead reckoning. The performing a site survey may include performing triage to a plurality of patients at different locations at the scene, and the method may further include, for a user of one of the plurality of mobile devices, subsequent to synchronizing to the common reference point, selecting one of a plurality of patients based on the data and treating the selected one. The method may further include synchronizing entered data relative to the selected one with the other plurality of mobile devices. The synchronizing may be performed on a wireless network connecting the mobile devices therebetween. The method may further include synchronizing entered data relative to the selected one with an emergency dispatch system. The method may further include synchronizing entered data relative to the site survey with an emergency dispatch system.

In another exemplary embodiment, a system may include a common reference point defined at a scene; a first responder with a first mobile device; and a plurality of subsequent responders each with one of a plurality of mobile devices; wherein the first responder defines the common reference point via the first mobile device and performs a site survey utilizing the first mobile device to capture location information and data for a plurality of points at the scene; and wherein the plurality of subsequent responders receive the location information and data on their respective mobile devices from the first mobile device. The system may further include a wireless network communicatively coupled to the first mobile device and the plurality of mobile devices. The system may further include an emergency dispatch system communicatively coupled to the wireless network and the first mobile device and the plurality of mobile devices.

In yet another exemplary embodiment, a mobile device includes a network interface; memory and a data store; a processor; and a local interface communicatively coupling the network interface, the memory, the data store, and the processor therebetween; wherein the processor is configured to: define a common reference point at a scene; receive location information and data for a plurality of points at the scene; and synchronize the location information and data with a plurality of additional mobile devices.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

In various exemplary embodiments, the present disclosure relates to electronic communication systems and methods for real-time location and information coordination between multiple people, such as, for example, in the context of medical emergencies. Specifically, the systems and methods may include a mobile device, a method of operating mobile devices, and a system including a plurality of mobile devices communicatively coupled therebetween for real-time location and information synchronization. In an exemplary embodiment, the systems and methods may be utilized in a medical emergency situation, i.e. for triage, enabling coordination of emergency personnel in an efficient manner. By way of the systems and methods described herein, a common reference point geographically defined, data is gathered with location referenced to the common reference point, and personnel may select patients based on the real-time gathered information. When particular patients are selected, the information may be updated to other personnel to avoid redundancy, and an administrator or incident commander may have unified visibility of all information including all patients and associated personnel.

Figure 1:
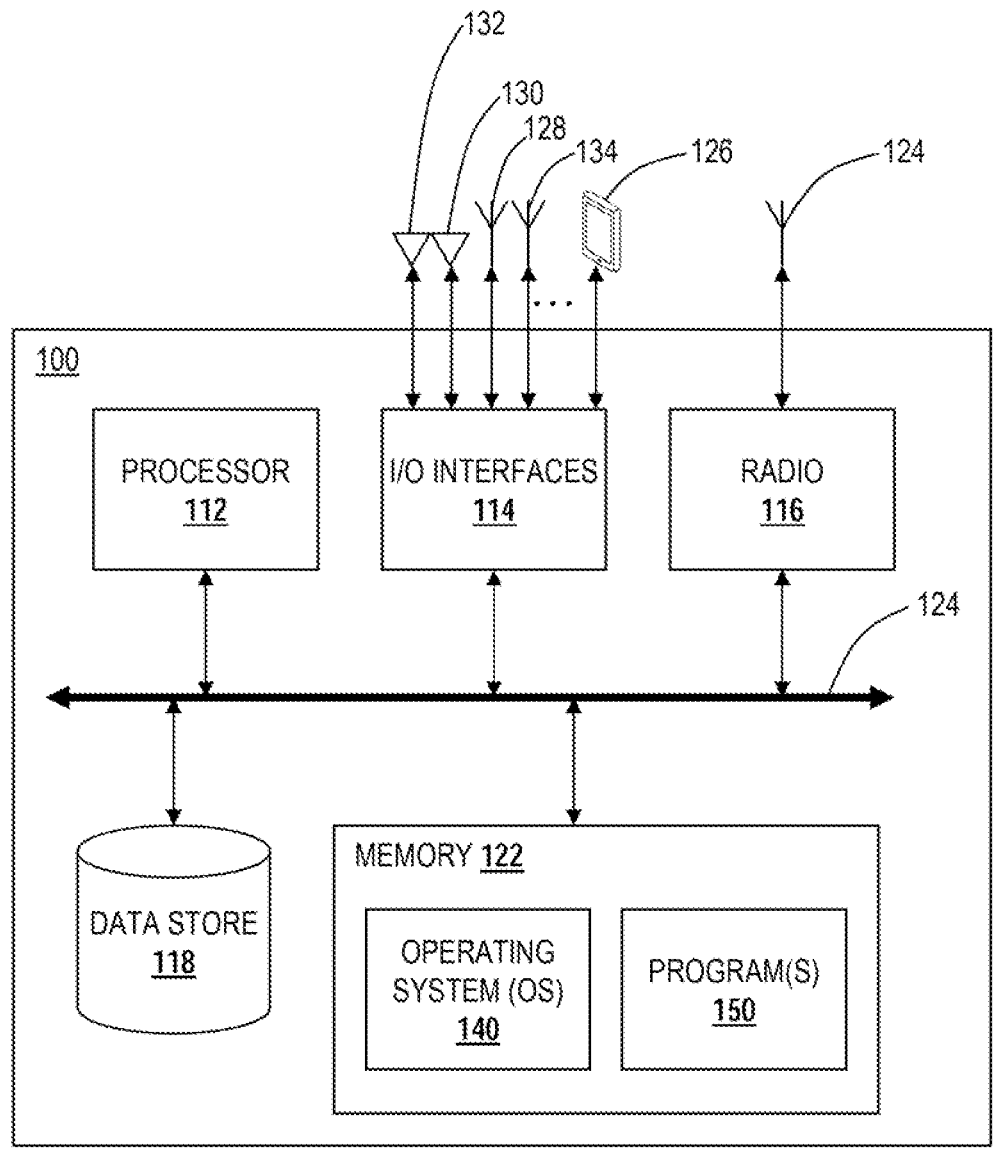
FIG. 1 is a block diagram of a mobile device, which may be used to implement the systems and methods for real-time location and information coordination between multiple people described herein.

Referring to FIG. 1, in an exemplary embodiment, a block diagram illustrates a mobile device 100, which may be used to implement the systems and methods for real-time location and information coordination between multiple people described herein. The mobile device 100 can be a digital device that, in terms of hardware architecture, generally includes a processor 112, input/output (I/O) interfaces 114, a radio 116, a data store 118, and memory 122. It should be appreciated by those of ordinary skill in the art that FIG. 1 depicts the mobile device 110 in an oversimplified manner, and a practical embodiment may include additional components and suitably configured processing logic to support known or conventional operating features that are not described in detail herein, such as power, batteries, etc. The components (112, 114, 116, 118, and 122) are communicatively coupled via a local interface 124. The local interface 124 can be, for example but not limited to, one or more buses or other wired or wireless connections, as is known in the art. The local interface 124 can have additional elements, which are omitted for simplicity, such as controllers, buffers (caches), drivers, repeaters, and receivers, among many others, to enable communications. Further, the local interface 124 may include address, control, and/or data connections to enable appropriate communications among the aforementioned components. In terms of housing and form factor, the mobile device 100 may include any of a tablet device, a smart phone, a personal digital assistance, a laptop computer, a net book computer, and the like.

The processor 112 is a hardware device for executing software instructions. The processor 112 can be any custom made or commercially available processor, a central processing unit (CPU), an auxiliary processor among several processors associated with the mobile device 110, a semiconductor-based microprocessor (in the form of a microchip or chip set), or generally any device for executing software instructions. When the mobile device 100 is in operation, the processor 112 is configured to execute software stored within the memory 122, to communicate data to and from the memory 122, and to generally control operations of the mobile device 100 pursuant to the software instructions. In an exemplary embodiment, the processor 112 may include a mobile optimized processor such as optimized for power consumption and mobile applications. The I/O interfaces 114 can be used to receive user input from and/or for providing system output to/from the mobile device 100. User input can be provided via, for example, a keypad, a touch screen 126, a radio frequency identification (RFID) device 128, a scroll ball, a scroll bar, buttons, a bar code scanner 130, and the like. System output can be provided via a display device such as a liquid crystal display (LCD), the touch screen 126, and the like. The I/O interfaces 114 can also include, for example, a serial port, a parallel port, a small computer system interface (SCSI), an infrared (IR) interface, a radio frequency (RF) interface, a universal serial bus (USB) interface, and the like. The I/O interfaces 114 can include a graphical user interface (GUI) that enables a user to interact with the mobile device 100. Additionally, the I/O interfaces 414 may further include an imaging device 132, i.e. camera, video camera, etc., and a global positioning satellite (GPS) receiver 134.

The radio 116 enables wireless communication to an external access device or network. Any number of suitable wireless data communication protocols, techniques, or methodologies can be supported by the radio 116, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols; wireless home network communication protocols; paging network protocols; magnetic induction; satellite data communication protocols; wireless hospital or health care facility network protocols such as those operating in the WMTS bands; Land Mobile Radio System (LMRS); GPRS; proprietary wireless data communication protocols such as variants of Wireless USB; and any other protocols for wireless communication. The data store 118 may be used to store data. The data store 118 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 118 may incorporate electronic, magnetic, optical, and/or other types of storage media.

The memory 122 may include any of volatile memory elements (e.g., random access memory (RAM, such as DRAM, SRAM, SDRAM, etc.)), nonvolatile memory elements (e.g., ROM, hard drive, tape, CDROM, etc.), and combinations thereof. Moreover, the memory 422 may incorporate electronic, magnetic, optical, and/or other types of storage media. Note that the memory 122 may have a distributed architecture, where various components are situated remotely from one another, but can be accessed by the processor 112. The software in memory 122 can include one or more software programs, each of which includes an ordered listing of executable instructions for implementing logical functions. In the example of FIG. 1, the software in the memory system 122 includes a suitable operating system (O/S) 140 and programs 150. The operating system 140 essentially controls the execution of other computer programs, and provides scheduling, input-output control, file and data management, memory management, and communication control and related services. The operating system 426 may be any of LINUX (or another UNIX variant), Android (available from Google), Symbian OS, Microsoft Windows CE, Microsoft Windows 7 Mobile, iOS (available from Apple, Inc.), webOS, Blackberry OS, and the like. The programs 150 may include various applications, add-ons, etc. configured to provide end user functionality with the mobile device 100. For example, exemplary programs 150 may include, but not limited to, a web browser, social networking applications, streaming media applications, games, mapping and GPS applications, electronic mail applications, financial applications, emergency dispatch and the like. In a typical example, the end user typically uses one or more of the programs 150 along with a network. In an exemplary embodiment, the programs 150 may include an application related to implementing the location and information coordination systems and methods described herein.

Figure 2:
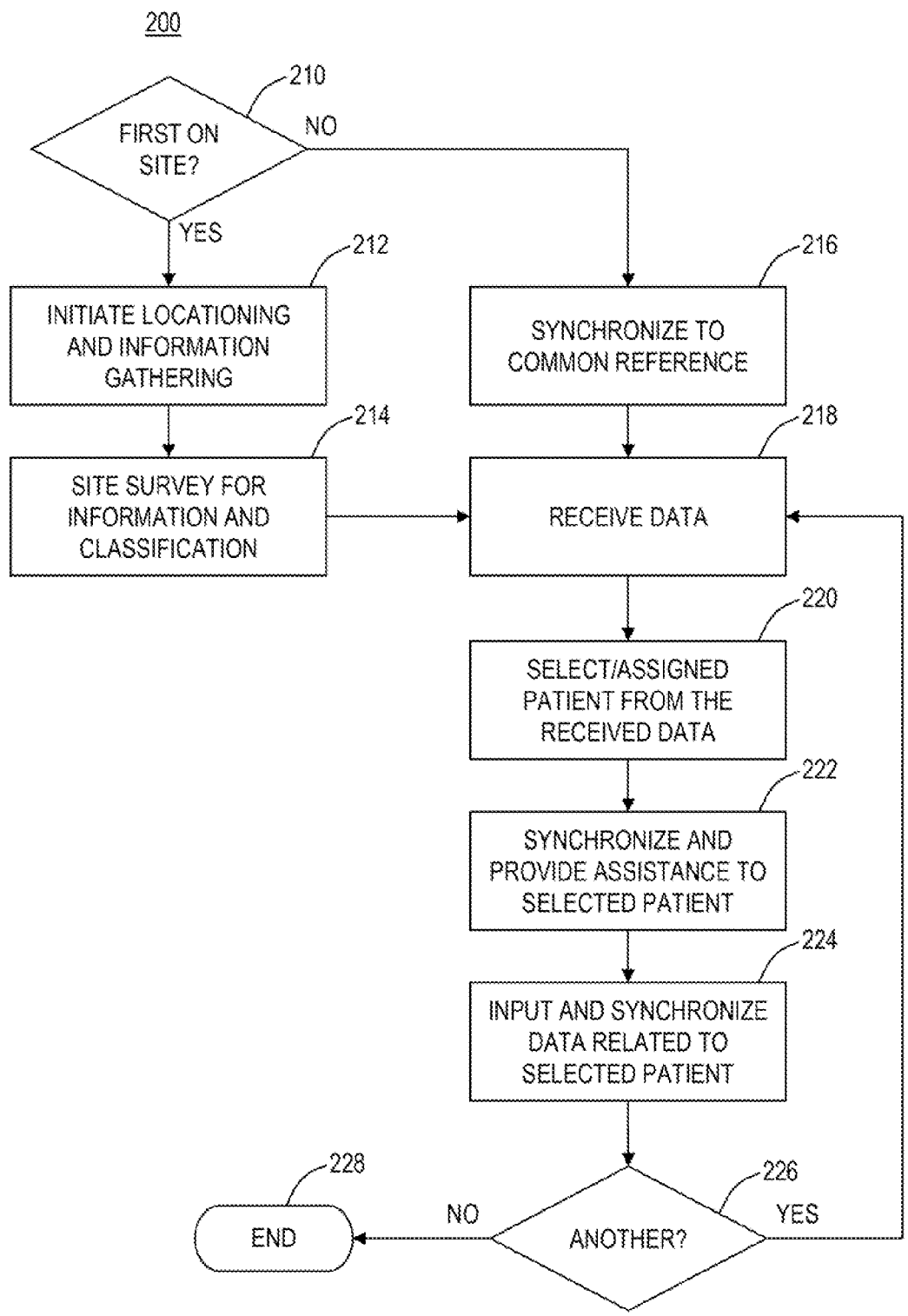
FIG. 2 is a flowchart of an exemplary method for location and information coordination.
Figure 3:
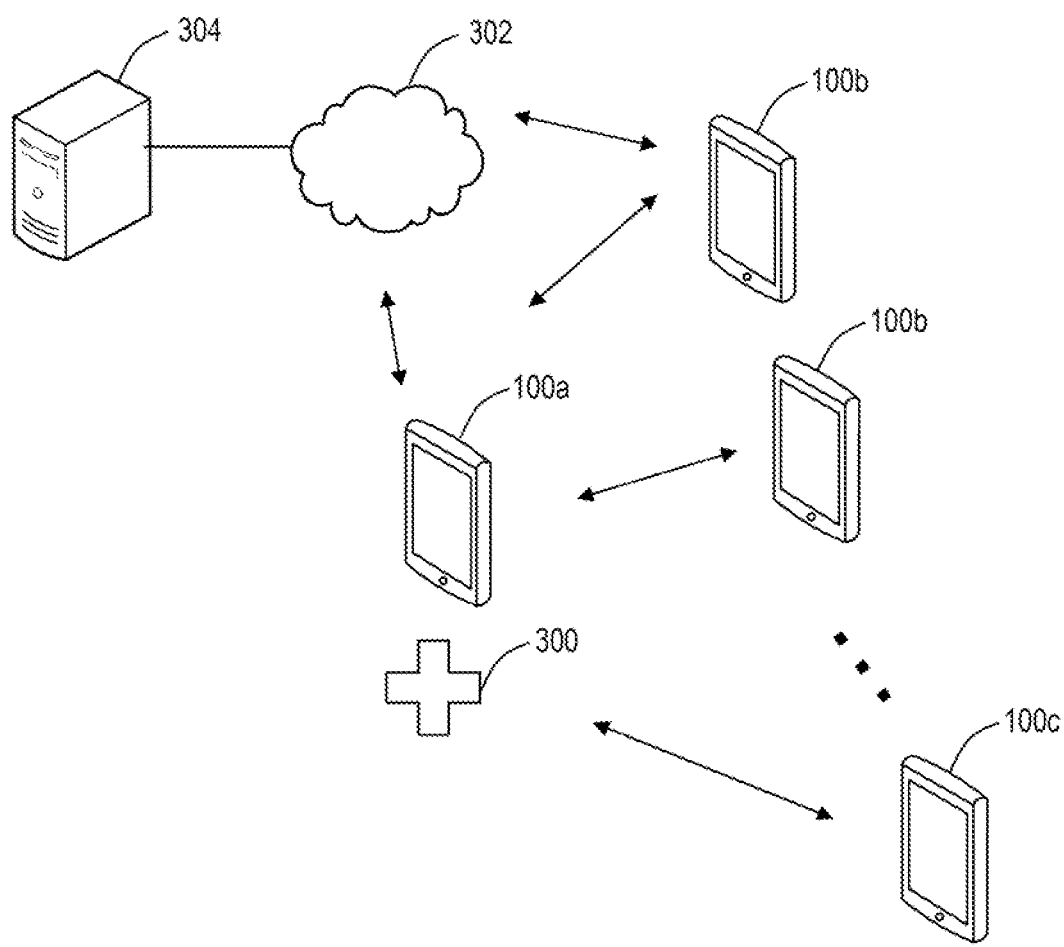
FIG. 3 is a diagram of an exemplary operation of the method for location and information coordination of FIG. 2.

Referring to FIGS. 2 and 3, a flowchart illustrates an exemplary method 200 for location and information coordination and a diagram illustrates an exemplary operation 202 of the method 200. The method 200 is described herein relative to a medical emergency context, and those of ordinary skill in the art will recognize the systems and methods for location and information coordination may be utilized in other contexts. When an emergency occurs (e.g., mass casualty, injuries, etc.), emergency personnel (e.g., paramedics, EMTs, etc.) are informed of the incident through a radio dispatch. Upon arrival to the scene the emergency personnel determine if they are the first on site (step 210). The first EMT to respond to the incident is assigned the task of being the triage EMT. The first EMT (or other personnel) initiates the process of locationing and information gathering (step 212). For example, in this role, the triage first emergency personnel may use an ambulance (or truck) as a reference truck. The initiation of the locationing and information gathering includes setting of a common reference point for the method 200. The initiation and the reference selection may be done through a push button event on the mobile device 100, such as, for example, after starting a locationing and information gathering application on the mobile device 100.

In the method 200, all location measurements and directions are referenced to the common reference point. To help reduce location error, the method 200 can also use various techniques in addition to utilizing the GPS receiver 134 on the mobile device 100. For example, the first EMT may have a GPS transmitter in an ambulance or truck allowing technologies like differential GPS. Differential GPS is an enhancement to GPS that uses fixed, ground-based reference stations to broadcast the difference between the positions indicated by the satellite systems and the known fixed positions. These stations broadcast the difference between the measured satellite pseudoranges and actual (internally computed) pseudoranges, and receiver stations may correct their pseudoranges by the same amount. Also, the method 200 can use technologies like dead reckoning for location tracking Dead reckoning is the process of estimating one's current position based upon a previously determined position, or fix, and advancing that position based upon known or estimated speeds over elapsed time, and course. For example, in the method 200, each user can go to common reference point (indicated on their mobile device 100 where each location is assigned a unique id) and calibrates his/her mobile device 100 to that common reference point.

Once the locationing and information gathering is initiated, the first EMT may perform a site survey for information gathering and classification (step 214). For example, the first EMT performs triage by going from patient to patient, denoting location, relevant information, type of injury, extent of injury (e.g., deceased, critical, severe, minor, etc.), etc. on the mobile device 100. During this site survey, the first EMT may also utilize the mobile device 100 to take pictures of each individual, to tag each individual with an identification device such as an RFID tag, a bar code, and the like, etc. Each individual's location is coordinated through the previously defined common reference point. The use of the common reference point reduces the location error since all synchronized mobile devices 100 will start from the same position. Upon completion of the site survey, the first EMT's mobile device 100 may include a screen that shows the location of each patient color coded by the extent of the injury. The method 100 may utilize a synchronization process described herein to enable real-time data coordination between the first EMT, subsequently arriving personnel, and an incident commander.

Upon arrival, each of the personnel who are not the first on site (step 210) will synchronize their respective mobile devices to the common reference point (step 216). Additionally, each of the personnel may also use the location error reducing procedures described herein such as differential GPS and dead reckoning. Once synchronized to the common reference point, each of the personnel will receive data through the mobile device 100. At this stage, the first EMT's mobile device 100 will contain all of the information based on the site survey, and each subsequently arriving responder will synchronize to the common reference point and download information from the first EMT's mobile device 100 or from another networked device as described in FIG. 3 with respect to the exemplary operation 202.

At this stage, each of the personnel will select or be assigned a patient to assist with based on the received data (step 220). The EMT may look at the mobile device 100 to determine what patient should be examined next. Alternatively, each EMT may be assigned a patient by an incident commander, the first EMT, etc. Once assigned, each EMT or the like will denote the assignment via their mobile device 100, e.g. click or touch an accept button. The EMT will utilize the location information received in their mobile device 100 to find the assigned person. For example, the EMT will utilize the location information along with a map displayed the mobile device 100, a picture of the assigned person on the mobile device 100 for identification, identification tags on the assigned person (RFID, bar code, etc.) and the like. When the EMT arrives at the assigned person the EMT notes (through a pull down) on the mobile device 100 that the patient is being served by the EMT (the EMT name or ID can be assigned to that patient through the pull down). The EMT will synchronize their input into the mobile device 100 with other mobile devices 100 and provide assistance to the assigned person (step 222). At this stage, the EMT may input data into their mobile device 100 relative to the assigned person and this data may be synchronized with other mobile devices 100 (step 224). For example, the data may include further diagnosis information, hospital routing information (patient 12 is going to hospital Z), and the like. Upon completion, if there are additional people (step 226), the EMT may be assigned another patient based on updated data (step 218) or the method 200 may end (step 228).

FIG. 3 illustrates the exemplary operation 202 of the method 200 illustrating communication processes between various user's mobile devices 100. The exemplary operation 202 is a geographical diagram with a common reference point 300 defined by a first EMT's mobile device 100*a*. The first EMT will perform the site survey and data collection following defining the common reference point 300. As such, the mobile device 100*a* will include all of the information based on the site survey. Subsequently arriving EMTs are denoted by mobile devices 100*b*. Additionally, an incident commander is denoted by a mobile device 100*c*. Note, data may be synchronized between each of the mobile devices 100*a*, 100*b*, 100*c* with the incident commander's mobile device 100*c* having greater visibility. For example, EMT's mobile devices 100*b* may not see any particular patient that has an assigned EMT whereas the incident commander's mobile device 100*c* may still retain visibility of all patients and which EMT is assisting with which patient.

The method 200 contemplates various processes for providing data synchronization between the mobile devices 100*a*, 100*b*, 100*c*. As described herein, each of the mobile devices 100*a*, 100*b*, 100*c* includes a wireless network interface. In an exemplary embodiment, the mobile devices 100*a*, 100*b*, 100*c* may form an ad-hoc network, such as using IEEE 802.11 or the like, and synchronize data sharing based on these connections. In another exemplary embodiment, the first EMT's mobile device 100*a* may serve as a hub with subsequent mobile devices 100*b*, 100*c* connecting thereto. In yet another exemplary embodiment, the mobile devices 100*a*, 100*b*, 100*c* may be communicatively coupled to a network 302 along with a server 304 that is also communicatively coupled to the network 302. For example, the network 302 may include a wireless network, a service provider network, an emergency personnel network, and the like. The server 304 may have a similar architecture as the mobile device 100 described in FIG. 1, and may be utilized as a central information hub to synchronize the various mobile devices 100a, 100b, 100c.

In an exemplary embodiment, the server 304 may be part of or communicatively coupled to an emergency dispatch system. Generally, an emergency dispatch system is a communication system that communicatively couples emergency personnel (fire fighters, police, EMT, paramedics, etc.) with emergency operators (e.g., 911 systems), hospitals, etc. The emergency dispatch system may provide information to the various mobile devices 100a, 100b, 100c via the server 304 or directly via a communications link over the network 302. Further, the emergency dispatch system may receive information from the various mobile devices 100a, 100b, 100c via the server 304 or directly via a communications link over the network 302. This linkage between the various mobile devices 100a, 100b, 100c and the emergency dispatch system further improves information and location coordination associated with the systems and methods described herein. In an exemplary embodiment, the emergency dispatch system may operate on the Land Mobile Radio System through the network 302 along with the various mobile devices 100a, 100b, 100c.

In an exemplary embodiment, each of the mobile devices 100a, 100b, 100c may be a so-called thick client with large memory and preloaded data in the large memory. For example, since emergency personnel are generally defined to a specific geographic location (e.g., a particular ambulance team may serve a particularly defined geography and hospital), it is envisioned that in addition to each of the mobile devices 100a, 100b, 100c including software to execute the method 200, the mobile devices 100a, 100b, 100c may include preloaded maps for use in the method 200. Additionally, the mobile devices 100a, 100b, 100c do not need to exchange large amounts of data therebetween. Each of the mobile devices 100a, 100b, 100c may store data locally for synchronization at a later time while only providing data updates (e.g., patient 12 has been assigned and worked on and is being sent to hospital Z, while storing data on the mobile device 100 for use later at the hospital Z). Advantageously, this reduces bandwidth requirements on wireless networks such as a Land Mobile Radio System since commands sent to the mobile device 100 need only instruct the device to display the mobile device 100 pre-stored data (maps, text, etc.).

Figure 4:
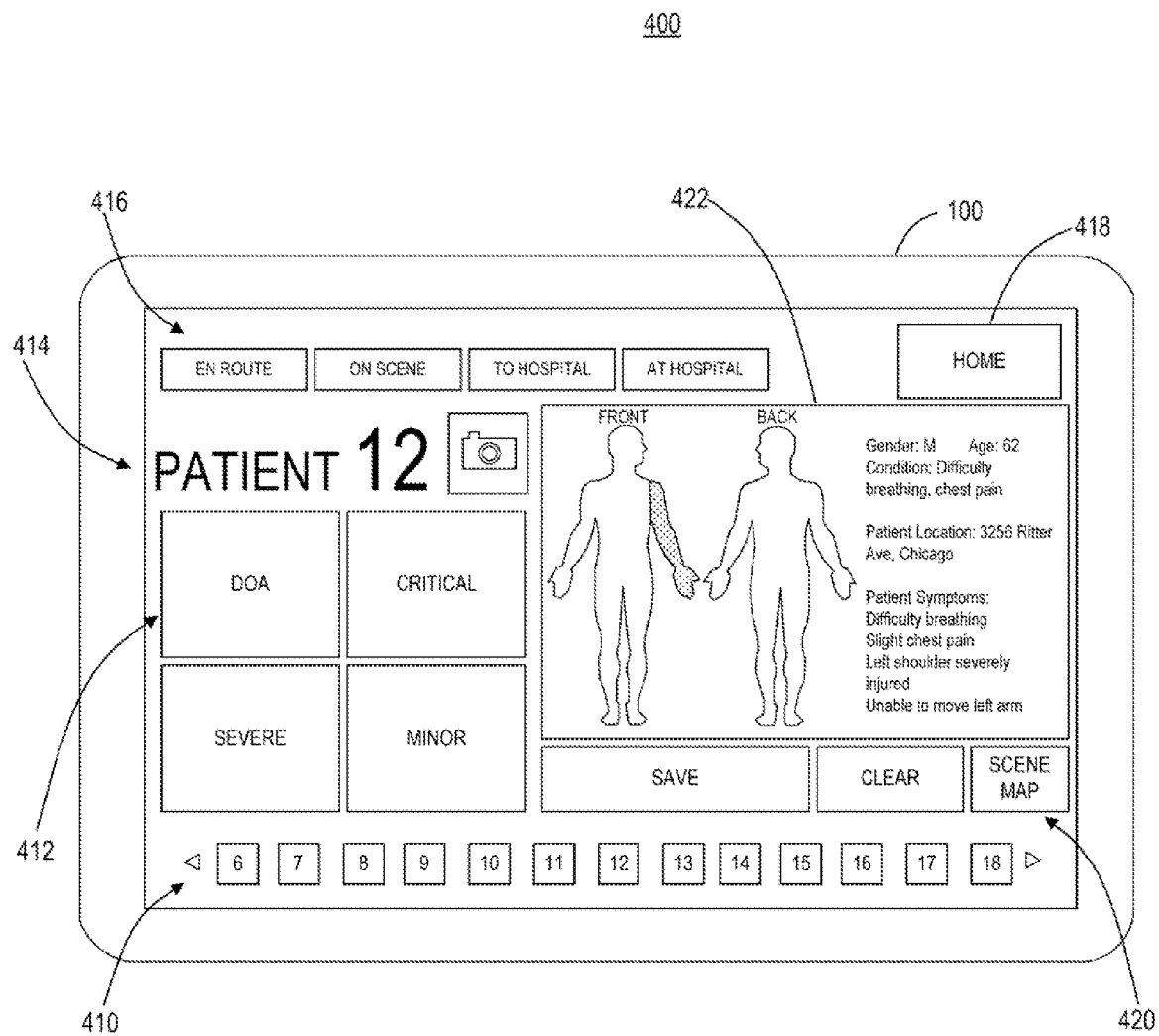
FIG. 4 is a screen shot of a graphical user interface for patient screen view on the mobile device of FIG. 1.
Figure 5:
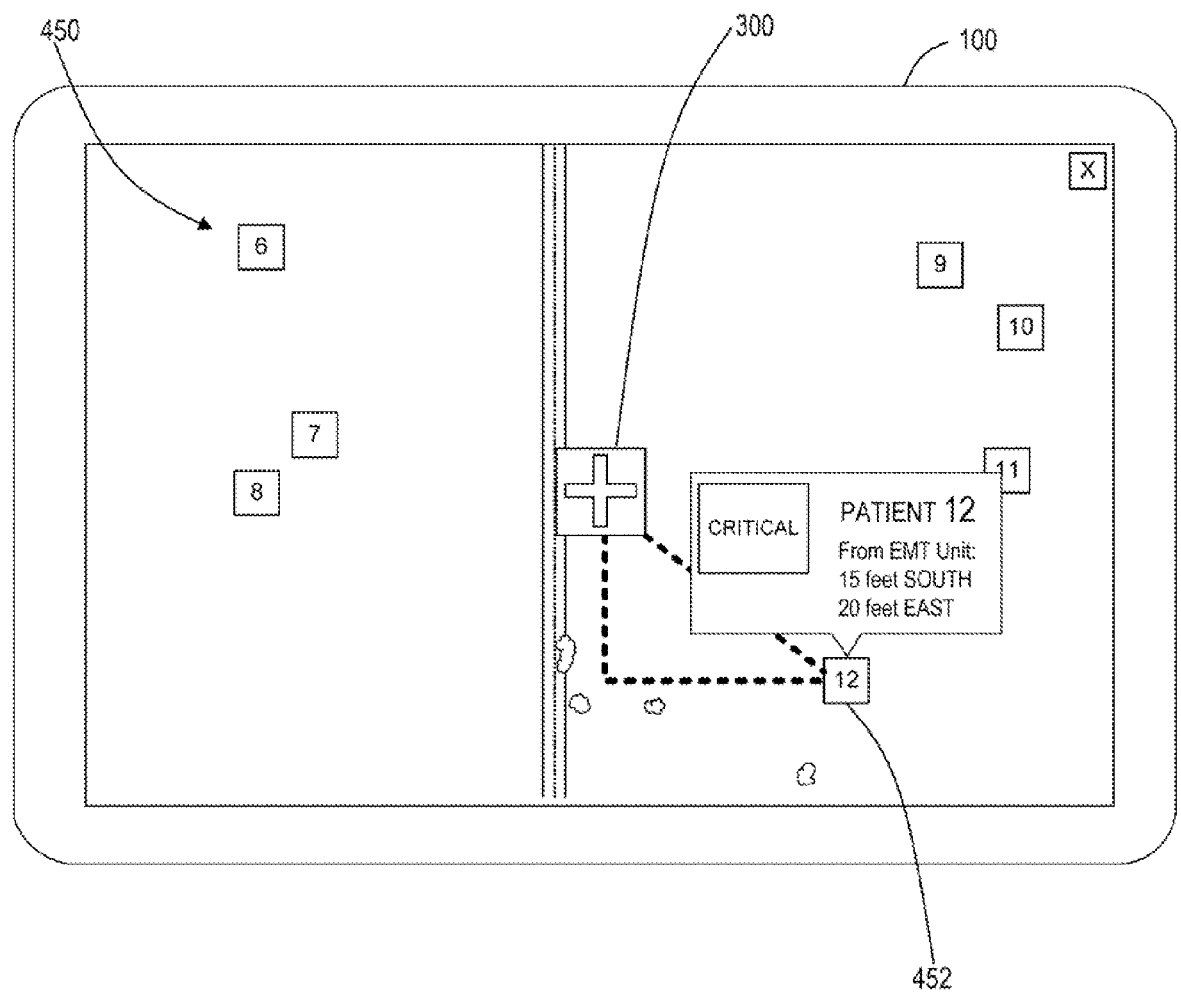
FIG. 5 is a screen shot of a graphical user interface for map screen view on the mobile device of FIG. 1.

Referring to FIGS. 4 and 5, in exemplary embodiments, screen shots 400, 402 illustrate exemplary graphical user interface (GUI) views on the mobile device 100 during the method 200. The screen shot 400 in FIG. 4 is an exemplary patient screen view on the mobile device 100. The screen shot 400 is an example of what each EMT may see while attending to a patient or what the first EMT may see while performing the triage via the site survey. The screen shot 400 includes various touch screen buttons for navigation and data entry. For example, the screen shot 400 includes a patient indicator line 410 listed numerically, status boxes 412 (e.g., DOA, critical, severe, minor) for injury classification, a currently viewed patient indicator 414 to denote which patient is being view or for which data is being entered, a process indicator 416 to indicate the status of the patient as well as actions taken on the patient (e.g., medications given, symptoms observed, electrocardiograph data taken), and the like. The screen shot 400 may also include navigation buttons such as a home icon 418 to navigate to a home screen and save, clear, and map buttons 420 to save data, clear data, and navigate to a map screen, respectively. Furthermore, the screen shot 400 may include a data screen 422 which may illustrate injuries graphically (e.g., patient 12 has the left shoulder and arm denoted as injured in the pictorial diagram in the data screen 422). The data screen 422 may also include text information that may be modified and entered. Touch screen button 410 may allow emergency personnel to see location of the patient injury (e.g., arm, leg, head, etc.) as well as patient information (e.g., facial image, injury image, injury description, name, age, etc.) for each patient 414. The screen shot 400 may also contain a barcode button allowing emergency personnel to scan items like triage tags drivers license, etc. It should be noted that the camera may also be used to decode and store bar code information. Note, the screen shot 400 may also include color coding for the status boxes 412, the injuries in the pictorial diagram in the data screen 422, etc.

FIG. 5 illustrates the screen shot 402 which is an exemplary map screen, i.e. navigated to by selecting the map button on the buttons 420. The map screen illustrates a map, e.g. which may be preloaded on the mobile device 100, along with synchronized data including the common reference point 300, a plurality of patients 450 each denoted by a distinct identification such as a number, and directions to a selected patient 452. The EMTs and incident commanders may utilize the map screen to determine which patient to treat (e.g., the plurality of patients 450 may be color coded on the map screen based on severity). As the selected patient 452 is taken by emergency personnel, information displayed on the screen shot 402 updating items like paramedic or EMT identification number and hospital where patient is being transported.

Advantageously, the systems and methods described herein enable location and information coordination in a real-time, synchronized fashion. In the context of a medical emergency, such as plane crash, bomb explosion, train wreck, earthquake, flood, etc.), emergency personnel may uses the systems and methods described herein to link data together via the mobile devices 100 to enable accurate location information and provide an efficient triage method to enable fast response. The systems and methods provide an automated method of addressing patients while enable an incident commander full visibility of the scene.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A method implemented on a mobile device, comprising:
defining a common geographic reference location point at a scene of multiple injured patients by a first responder;
performing a site survey of each patient at the scene by the first responder to gather data and location information with respect to the reference location point;
sharing the injury data and location information of the patients in real-time to a plurality of subsequent responder mobile devices;
for each of subsequent responder mobile device, selecting one of the patients to attend from the site survey; and
for each subsequent responder mobile device, the selection with the other mobile devices in real-time, avoiding redundant assistance to one patient;

further comprising updating all mobile devices with further diagnosis information and hospital routing information of each patient, wherein updating includes assigning a responder to another patient after that responder's current patient has been attended to.

2. The method of claim 1, wherein selecting includes each mobile device of the subsequent responders starting from the reference location point and directing its responder to the selected patient by using the site survey referenced to the reference location point.

3. The method of claim 1, wherein the site survey shows the location of each patient color coded by the extent of their injury.

4. The method of claim 1, wherein the site survey is shown as a map on a display of a mobile device.

5. The method of claim 1, further comprising viewing all patients and which responder is assisting with which patient by an incident commander.

6. The method of claim 1, further comprising the mobile devices forming an ad-hoc wireless communication network.

7. The method of claim 6, wherein the mobile device of the first responder serves as a communication hub with the subsequent responder's mobile devices.

8. The method of claim 1, wherein selecting includes assigning a responder to a patient by an incident commander based on the injury data.

9. The method of claim 8, further comprising:
displaying on a mobile device a status box for injury classification and treatment actions of a patient.

10. The method of claim 9, wherein displaying includes providing a graphical representation of the injuries to a patient.

11. The method of claim 8, wherein sharing include sharing injury data relative to the selected patient with an emergency dispatch system that communicatively couples emergency responders with emergency operators.

12. The method of claim 1, further comprising:
providing the further diagnosis information by the mobile device to the hospital where the patient is being routed.

13. A system, comprising:
a common geographic reference location point at a scene of multiple injured patients;
a first responder comprising a first mobile device; and
a plurality of subsequent responders each comprising one of a plurality of mobile devices;
wherein the first responder defines the reference location point via the first mobile device and performs a site survey of each patient at the scene by utilizing the first mobile device to capture location information with respect to the reference location point and injury data for each patient at the scene; and
wherein the plurality of subsequent responders receive the location information and data on their respective mobile devices from the first mobile device in real-time, select a location of one of the patients to attend from the site survey, and report the selection with the other mobile devices in real-time to avoid redundant assistance to one patient;
further comprising updating all mobile devices with further diagnosis information and hospital routing information of each patient, wherein updating includes assigning a responder to another patient after that responder's current patient has been attended to.

14. The system of claim 13, further comprising:
an ad-hoc wireless network communicatively coupled the first mobile device and the plurality of mobile devices.

15. The system of claim 13, further comprising:
an emergency dispatch system communicatively coupled to emergency responders, emergency operators, and the mobile devices.

16. A mobile device, comprising:
a network interface;
memory and a data store;
a processor; and
a local interface communicatively coupling the network interface, the memory, the data store, and the processor there between;
wherein the processor is configured to:
define a common geographic reference location point at a scene of multiple injured patients;
perform a site survey of each patient at the scene to gather injury data and location information with respect to the reference location point;
share location information and injury data for the patients at the scene in real-time with a plurality of subsequent responder mobile devices for the; mobile devices to select one of the patients to attend from the site survey and report the selection with the other mobile devices in real-time to avoid redundant assistance to one patient;
further comprising updating all mobile devices with further diagnosis information and hospital routing information of each patient, wherein updating includes assigning a responder to another patient after that responder's current patient has been attended to.

\* \* \* \* \*